(12) United States Patent
Brandau et al.

(10) Patent No.: US 6,740,077 B1
(45) Date of Patent: May 25, 2004

(54) IMPLANT WITH PERMEABLE ELEMENT

(75) Inventors: Wolfgang Brandau, Münster (DE); Alfons Fischer, Essen (DE); Thomas Sawitowski, Essen (DE); Günter Schmid, Velbert (DE)

(73) Assignee: AlCove Surfaces GmbH, Essen (DE)

( * ) Notice: Subject to any disclaimer, the term of this patent is extended or adjusted under 35 U.S.C. 154(b) by 0 days.

(21) Appl. No.: 09/913,942

(22) Filed: Aug. 20, 2001

(30) Foreign Application Priority Data

Feb. 18, 1999 (DE) .......................................... 199 07 006
Mar. 9, 1999 (DE) .......................................... 199 10 188
Oct. 8, 1999 (DE) .......................................... 199 48 783

(51) Int. Cl.[7] .................................................. A61K 9/22
(52) U.S. Cl. .................................................. 604/892.1
(58) Field of Search ........................ 604/890.1–892.1, 604/93.01, 288.01; 424/422–424

(56) References Cited

U.S. PATENT DOCUMENTS

| | | |
|---|---|---|
| 3,732,865 A | * 5/1973 | Higuchi et al. .......... 604/892.1 |
| 3,760,804 A | * 9/1973 | Higuchi et al. .......... 604/892.1 |
| 3,929,132 A | * 12/1975 | Higuchi .................. 604/892.1 |
| 3,944,064 A | 3/1976 | Bashaw et al. |
| 3,946,734 A | 3/1976 | Dedrick et al. |
| 4,218,255 A | 8/1980 | Bajpai et al. |
| 5,000,957 A | 3/1991 | Eckenhoff et al. |
| 5,008,112 A | 4/1991 | DePrince et al. |
| 5,062,841 A | 11/1991 | Siegel |
| 5,082,668 A | 1/1992 | Wong et al. |
| 5,320,616 A | 6/1994 | Magruder et al. |
| 5,769,823 A | 6/1998 | Otto |
| 5,897,528 A | * 4/1999 | Schultz .................. 604/500 |
| 5,908,414 A | 6/1999 | Otto et al. |

FOREIGN PATENT DOCUMENTS

| | | |
|---|---|---|
| CH | 580 961 | 10/1976 |
| CH | 580 961 A | 10/1976 |
| DE | 197 04 497 C1 | 2/1997 |
| DE | 197 04 497 | 11/1997 |
| EP | 0 875 218 A2 | 4/1998 |

* cited by examiner

Primary Examiner—LoAn H. Thanh
(74) Attorney, Agent, or Firm—Nixon Peabody LLP; David S. Safran

(57) ABSTRACT

An implant is suggested having a receptacle space for a therapeutic agent, which can leave the receptacle space through a permeable element. For exact dosage, an open-pore diffusion element is suggested as the permeable element, wherein the pore walls are chemically modified for control of the diffusion.

26 Claims, 4 Drawing Sheets

IMPLANT WITH PERMEABLE ELEMENT

Figure 1:
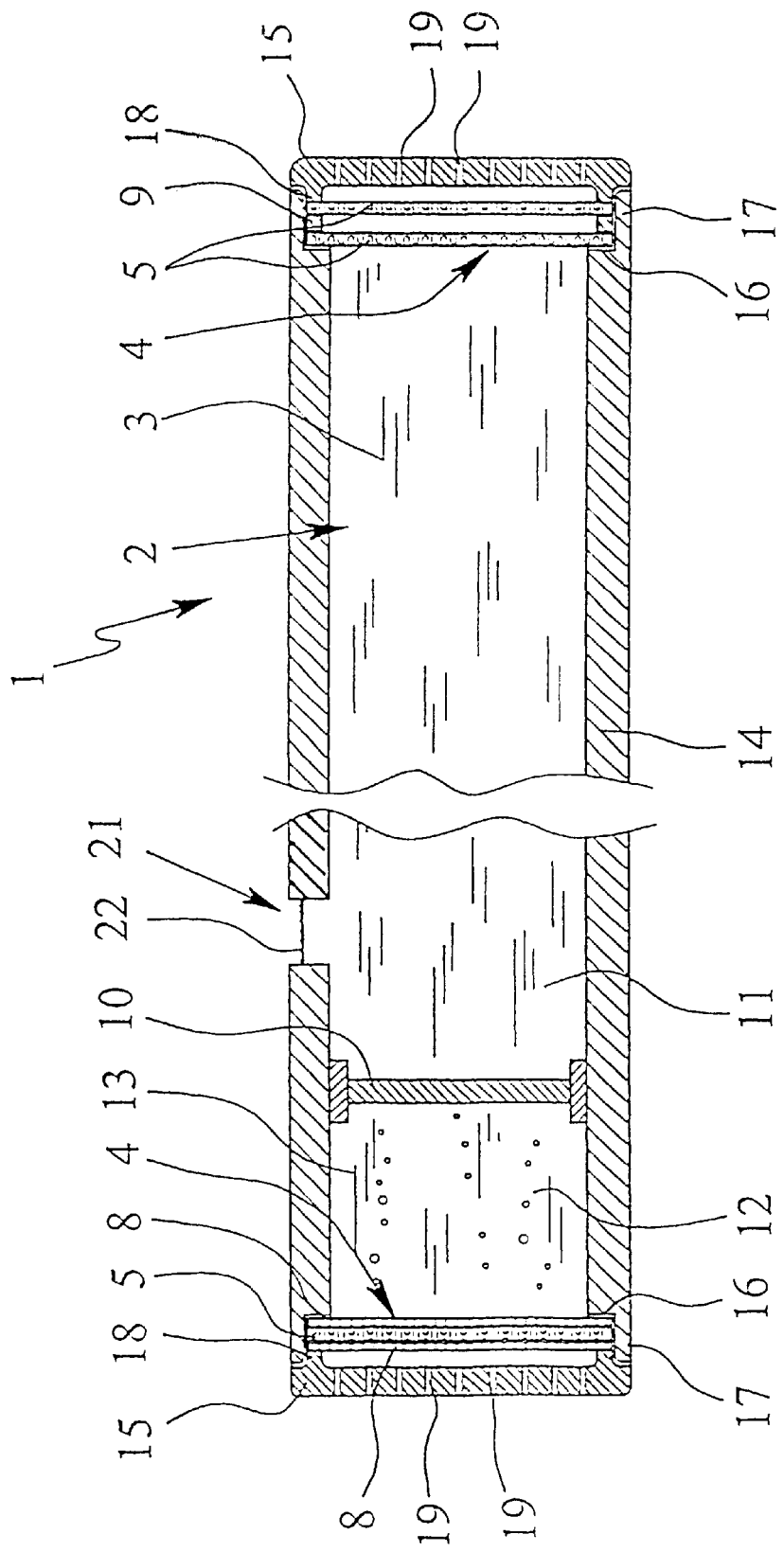

The present invention relates to an implant according to the preamble of claim 1.

Here, the term "implant" is to be first understood in a narrower sense as an element to be inserted at least temporarily in the body of an animal or a human, which, for example, can exclusively exercise therapeutic functions, but can also exercise support and/or joint functions. In a broader sense, however, elements which can be brought into contact with the body externally, particularly temporarily, or the like are also meant here.

The term "therapeutic agent" here particularly refers to drugs and/or pharmaceuticals on one hand and medications and other substances to be supplied to the human or animal body on the other hand. In particular, all of the therapeutic agents mentioned in EP-A-0 875 218 as "medications" and/or receptor agonists, receptor antagonists, enzyme inhibitors, neurotransmitters, cytostatics, antibiotics, hormones, vitamins, metabolic substrates, anti-metabolites, diuretics, and the like can be considered a therapeutic agent.

An implantable infusion pump is known from DE-C-197 04 497, which represents the most relevant prior art, in which a drug is driven out of a receptacle space by means of a propellant and released into the body via a catheter. A throttle path is provided between the receptacle space and the catheter. The throttle path is formed by a perfusion plate which is provided with multiple bores of a magnitude of 1 $\mu$m. The bores are made in the perfusion plate by means of a laser beam, the perfusion plate consisting of ceramic, for example.

The drug flows through the bores of the perfusion plate into the adjacent catheter due to the pressure produced by the propellant in the known infusion pump. In this case, the perfusion plate acts as a throttle point, i.e. the amount of drug flowing through per unit of time depends on the pressure of the propellant and the fluidic properties of the drug. During this flow through the perfusion plate, the interaction between the bores of the perfusion plate and the drug expelled is restricted to the throttle effect of the bores, i.e. to a quasi-mechanical influence relative to the flow. It is hereby disadvantageous that the amount of drug released and/or flowing through per unit of time depends on the pressure produced by the propellant, so that unavoidable pressure changes often lead to undesired oscillations of the release speed. Another disadvantage is that the bores of the perfusion plate or other throttles can at least partially clog due to deposition of substances penetrating them. This leads to an undesired and undefined change of the throttle effect and thereby to an undesired influence on the amount of drug released and/or flowing through per unit of time.

The object of the present invention is to provide an implant which, particularly even for the smallest of quantities, allows preferably pressure-independent release per unit of time of a therapeutic agent and/or at least one active substance of the therapeutic agent, wherein, in particular, the problem of deposition of materials can be prevented, at least as much as possible.

The above object is achieved by an implant according to claim 1. Advantageous embodiments are objects of the subclaims.

A fundamental idea of the present invention is to provide a diffusion element with open pores, so that only diffusion is allowed, but not free flow and/or to provide a chemical modification of pore walls so that an interaction, which is preferably selective in regard to passage, can be achieved with a therapeutic agent and/or at least one active substance of the therapeutic agent. Thus, a released amount per unit of time can be reached which is at least largely independent from the pressure acting on the therapeutic agent. As a consequence, a more exact dosing is possible, particularly for small released amounts. Furthermore, clogging and/or blockage of the permeable element is prevented, at least as much as possible, in the embodiment according to the invention.

According to a preferred embodiment, the pores of the permeable element have, on average, a diameter of 20 nm to 250 nm. Free flow through the pores is prevented, at least as much as possible by this pore size, so that the desired independence from pressure of the released amount per unit of time occurs. In addition, this pore size prevents the entrance of bodily substances, such as proteins, into the pores and therefore into the implant.

The walls of the pores of the permeable element can, for example, be implemented as hydrophilic or hydrophobic and/or be provided, at least partially, with functional groups for chemical modification. Thus, it is possible that, e.g. only the therapeutic agent or only one active substance of the therapeutic agent can pass through the pores, so that selective interaction between the chemically modified pore walls and the therapeutic agent and/or at least one active substance of the therapeutic agent can be achieved. This selective interaction can prevent undesired clogging and/or blockage of the pores.

The permeable element of the proposed implant is preferably produced essentially from metal oxide and/or ceramic material. Very simple production and formation of highly uniform pores in the permeable element is made possible preferably by an artificial, particularly electrolytic, oxidation (anodization), particularly of aluminum. In principle, all so-called valve metal oxides are suitable for this purpose, such as aluminum oxide, tantalum oxide, iron oxide, tungsten oxide, and/or titanium oxide, as well as magnesium oxide.

The diameter of the pores and the surface density of the pores, i.e. the number of pores per area, can be varied by varying the electrical voltage during anodization. As a consequence, the shape of the pores can be controlled within wide ranges. In particular, the pores are, at least essentially, formed as tubes and extend from the surface of the permeable element essentially perpendicularly through the permeable element, wherein the cross-section of the pores and/or their openings can be portionally reduced with respect to diameter and/or area in order to achieve desired characteristics.

A particularly preferred embodiment is characterized by a second passage opening associated with the receptacle space, in which a permeable element/membrane-like separating element is inserted as well, so that the therapeutic agent or at least one active substance of the therapeutic agent can leave the receptacle space through the one opening/the permeable element inserted in the opening and substances can enter into the receptacle space from outside through the other passage opening/the permeable or separating element inserted in the permeable element. This quasi-double osmosis can be achieved by desired, different formation and/or chemical modification of the permeable elements. The substances, such as water or the like, penetrating from the outside into the receptacle space can compensate for a reduction in volume of the therapeutic agent in the receptacle space, so that neither low pressure, interfering with the release of the therapeutic agent from the receptacle space nor a pressure difference destroying the permeable element can occur.

If necessary, a wall element can be provided to divide the receptacle space, in order to prevent mixing and/or dilution of the therapeutic agent by the substances penetrating into the receptacle space.

Figure 2:
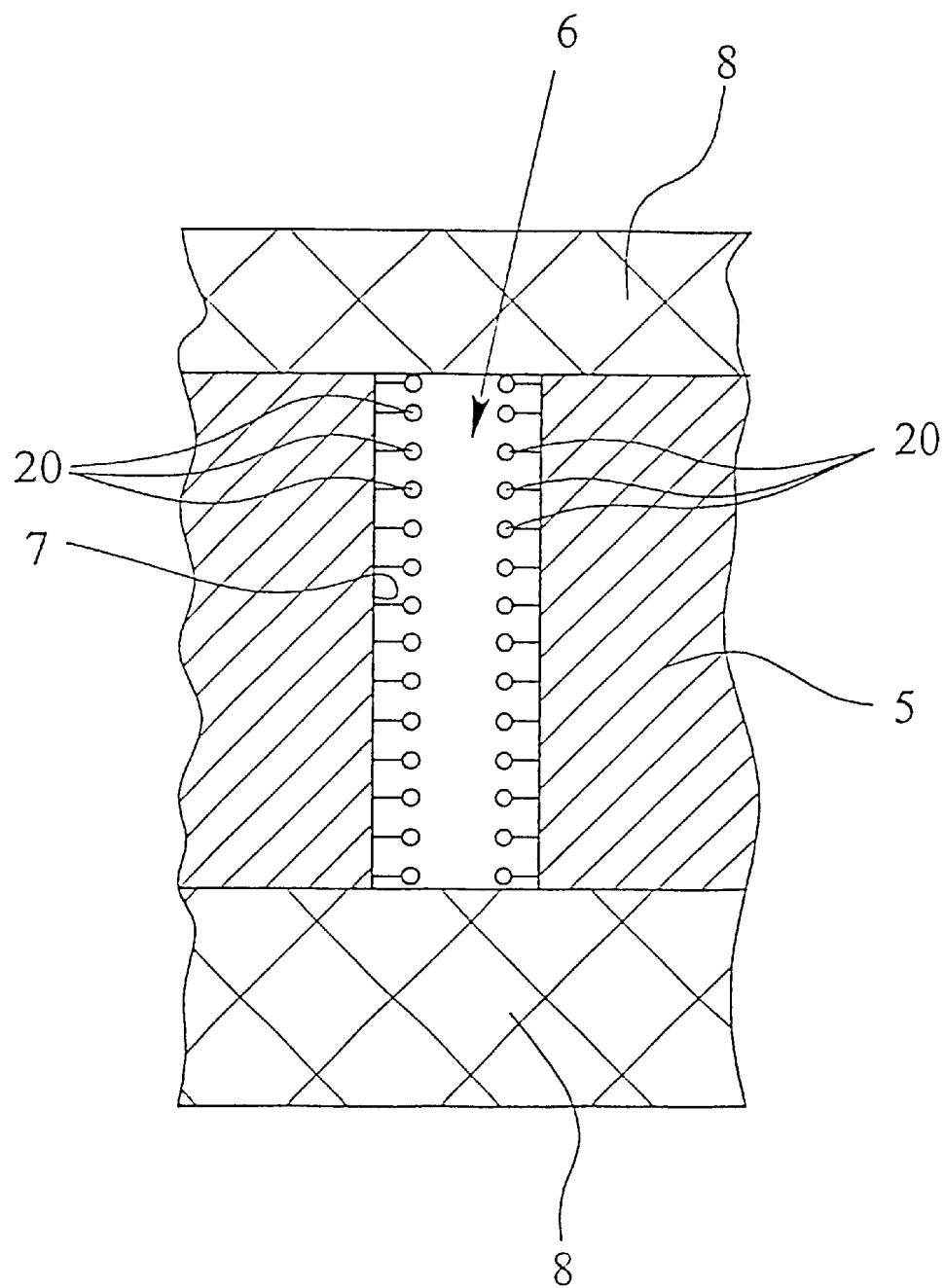
Figure 3:
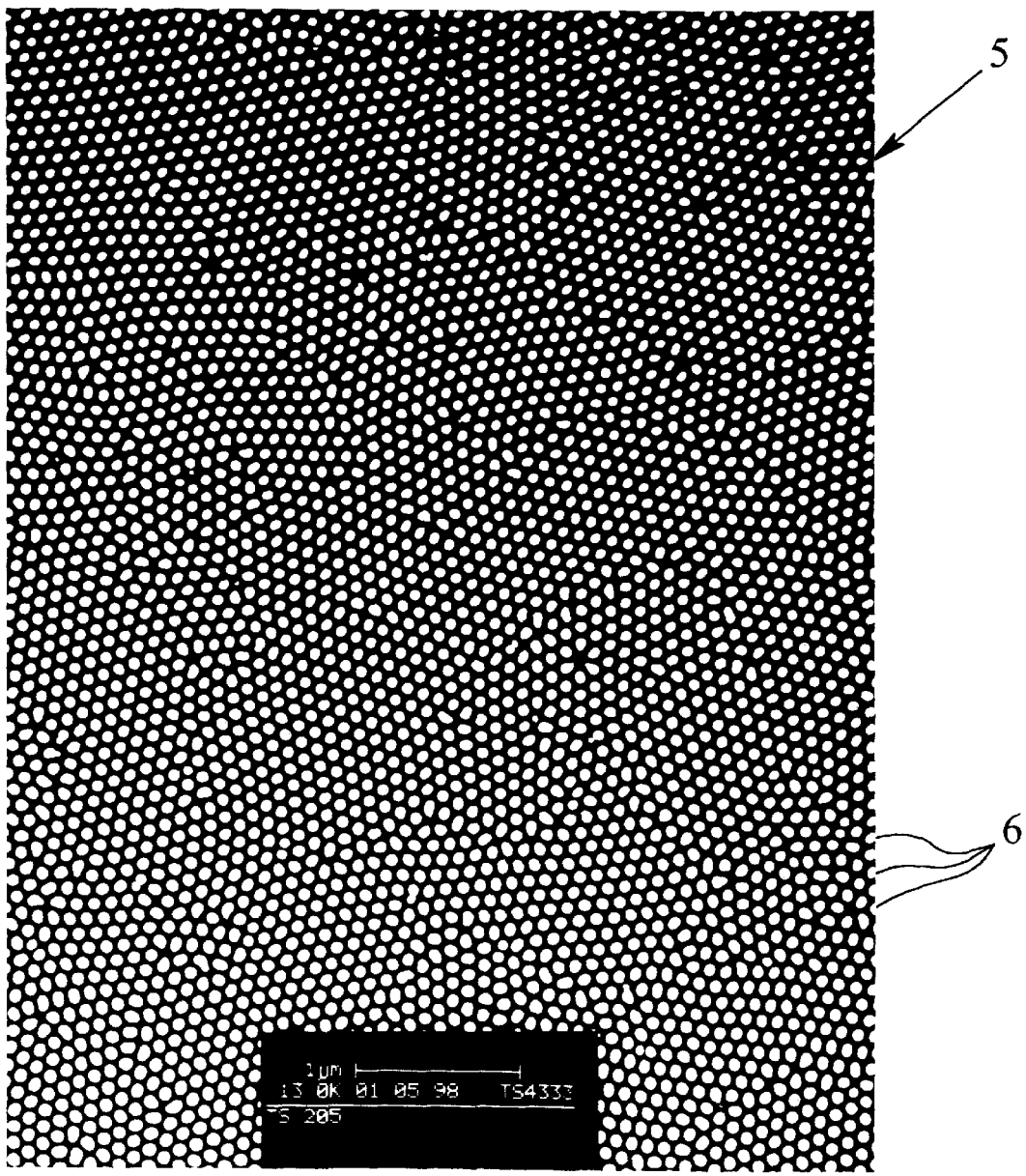
Figure 4:
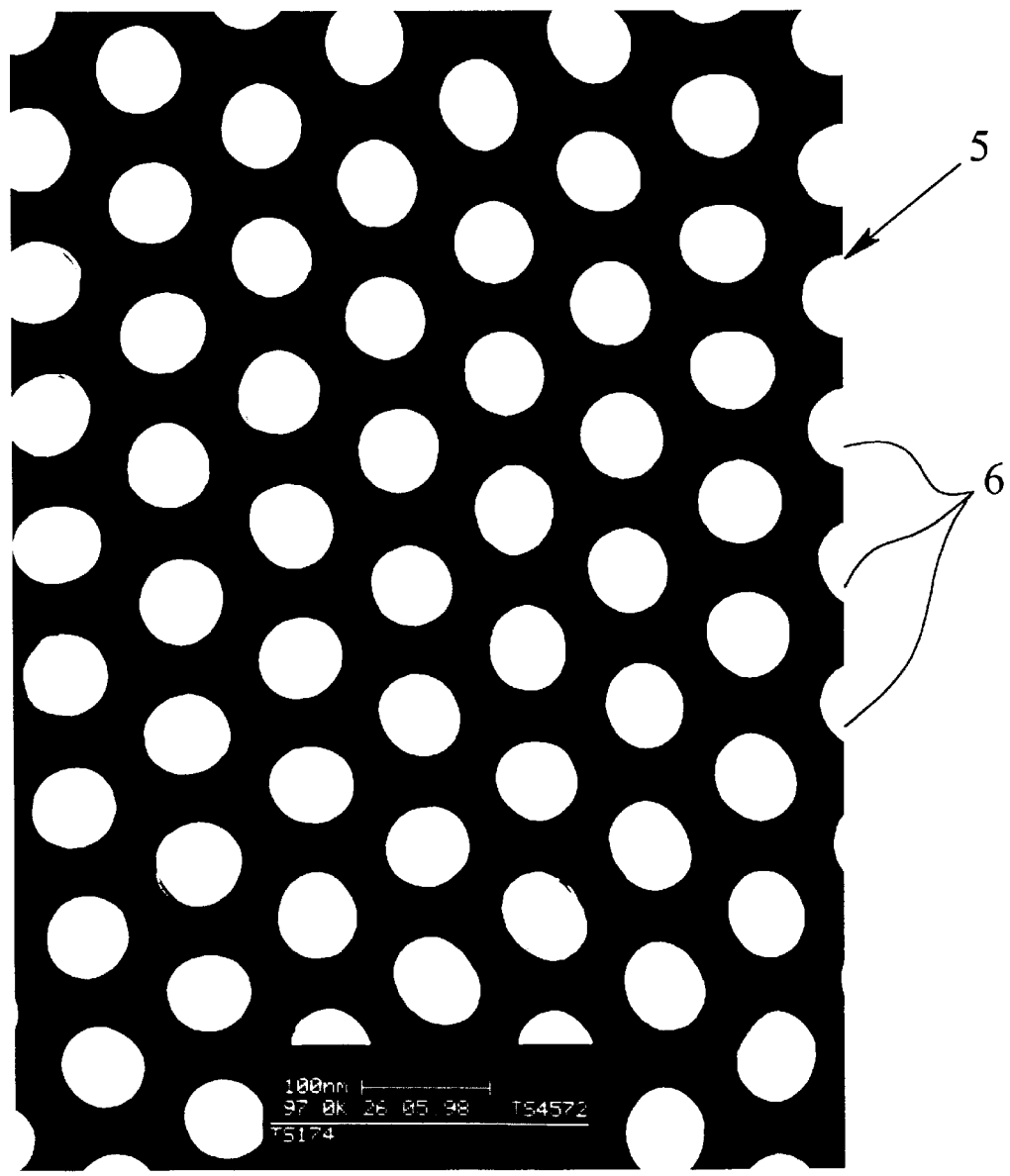

In the following, the present invention will be described in more detail with reference to the drawings of a preferred exemplary embodiment. It shows:

FIG. 1 a schematic sectional view of a proposed implant;

FIG. 2 a schematic sectional view of a pore of a permeable element of the implant according to FIG. 1 supported on both sides; and FIGS. 3, 4 electron microscope exposures in different enlargements of an aluminum oxide film having pores.

FIG. 1 shows a schematic sectional view of a proposed implant 1. In the exemplary embodiment illustrated, the implant 1 has an essentially cylindrical shape. However, any other desired shapes, such as flat or disk shapes, are also possible.

The implant 1 has a receptacle space 2 for receiving a therapeutic agent 3. Regarding the therapeutic agent 3, attention is drawn to the definition at the beginning.

The implant comprises at least one passage opening 4, which, in this case in particular, is located in the region of an end/face of the implant 1. At least one permeable element 5 is associated to the passage element 4. In the example illustrated, two permeable elements 5 are, for reasons of reliability, inserted one after another in the right-hand passage opening 4, which is in contact with the therapeutic agent 3 in order to reliably prevent undesired and/or uncontrolled leakage of the therapeutic agent from the receptacle space 2 should one permeable element 5 break or be damaged. The two permeable elements 5 are identically formed in the exemplary embodiment, wherein, however, different formations are also possible.

In the following, the preferred embodiment of the permeable element 5 will be described in more detail with reference to the schematic sectional view through a permeable element 5 according to FIG. 2.

The permeable element 5 is permeable to the therapeutic agent 3 or at least one active substance of the therapeutic agent 3. For this purpose, the permeable element 5 is preferably formed as open-pored. FIG. 2 shows a pore 6 in partial sectional view. The permeable element 5 comprises a plurality of these types of pores 6, through which the therapeutic agent 3/at least one active substance of the therapeutic agent 3 can pass, in particular only diffuse from the receptacle space 2 to the outside.

It can be inferred from FIG. 2 that the pores 6 extend essentially perpendicularly through the main plane of extension of the permeable element 5, which runs horizontally in FIG. 2. The pores 6 correspondingly run essentially parallel to one another. In particular, the pores 6 are essentially uniform, in particular, essentially circularly cylindrical.

FIGS. 3 and 4, which depict electron microscope exposures of the surface of a permeable element 5 in different enlargements, illustrate how uniformly the tube-shaped pores 6, which appear white, are distributed and formed.

The surface density of the pores 6 is preferably approximately $10^8$ to $10^{11}$/cm$^2$. The average pore diameter is preferably a maximum of 500 nm, particularly 20 nm to 250 nm.

In the depicted exemplary embodiment, it can be inferred from FIG. 2 that the pores 6 have an essentially constant cross-section over their entire extension through the permeable element 5. In this case, the pore walls 7 of the pores 6 thus each essentially form a cylinder shell surface.

The thickness of the permeable element 5 is low, particularly less than 50 µm, and preferably a maximum of 5 µm. Correspondingly, a proportionally lower diffusion/penetration resistance results for the therapeutic agent 3 or at least one active substance of the therapeutic agent 3.

The permeable element 5 consists preferably at least essentially of aluminum oxide, which is, in particular, electrolytically deposited and/or formed. For example, an aluminum film which is carried by a carrier (not shown) is electrically oxidized (anodized) and then detached from the carrier in order to obtain the permeable element 5. During the electrolytic oxidation, the diameter of the pores 6 can be changed very easily by appropriate adjustment of the voltage applied. Here, a diameter of 1.2 to 1.4 nm per 1 V of anodic voltage results.

The material of the permeable element 5/non-oxidized material, such as aluminum, can also be applied onto the carrier (not shown), e.g. alternatively by plasma coating and, if necessary, then be oxidized.

The production of the permeable element 5 is, however, not restricted to the preceding examples, for example, oxidation of an appropriate surface coating of the carrier (not shown), which would then be detached, could also be considered.

Furthermore, the material for the permeable element is not restricted to aluminum oxide, but, in general, all so-called valve metal oxides and magnesium oxide can be used. In addition to these oxides, ceramic materials, which essentially comprise or allow, respectively an appropriate formation of pores, are, in general, also suitable.

Since its thickness is low, the permeable element 5 has an intrinsic stability which is, at most, low. It is therefore preferably supported by at least one, e.g. grating-like support element 8 on at least one side. FIG. 2 shows an alternative embodiment, in which the permeable element 5 is supported on both sides by a support element 8, i.e. is held between two support elements 8.

In the example illustrated according to FIG. 1, the implant 1 comprises a second opening 4, which is preferably positioned on the other end here, the left end/opposite to the first opening 4. Preferably, a permeable element 5 according to the preceding description is associated to this second passage opening 4 as well. In particular, this permeable element 5 is also inserted in the passage opening 4, so that substance interchange between the receptacle space 2 of implant 1 and the external space surrounding the implant 1 is also only possible through the permeable element 5.

In the illustrated example according to FIG. 1, only a single permeable element 5 is associated to the second passage opening 4; the permeable element 5 being supported on both sides by support elements 8, corresponding to the illustration in FIG. 2.

On the other hand, as an alternative embodiment, the two permeable elements 5 in the first opening 4 on the other side are kept at a distance from one another by a spacer 9, which is preferably ring-shaped. In addition, support elements 8 (not shown) or other reinforcing elements can be associated to the permeable elements 5 in order to ensure sufficient support of the permeable elements 5, particularly in the case of insufficient intrinsic stability and load capacity.

As can be inferred from FIG. 1, the implant 1 comprises a wall element 10, formed here essentially as a piston, which divides the receptacle space 2 into a first space portion 11 and a second space portion 12, wherein the first space portion 11 is connected to the first or, respectively one passage opening 4, and the second space portion 12 is connected with the second or, respectively another passage opening 4. The wall element 10 is piston-like movably mounted here in the receptacle space 2. However, an membrane-like or bellows-like formation of the wall element 10, for example, is also possible if it is appropriately flexible, movable and/or displaceable.

The therapeutic agent 3 is preferably only filled into the first space portion 11. Another agent, referred to here as the compensation agent 13, is preferably contained in the second space portion 12. The function of the compensation agent 13 will be described in more detail later.

A simple filling of the therapeutic agent 3 and the optionally provided compensation agent 13 into the implant 1/receptacle space 2 is made possible in a preferred embodiment in that at least one of the passage openings 4 is initially still open or can be opened. The associated permeable element 5 is then only inserted in the passage opening 4 after the receptacle space 2 has been filled.

Particularly in the cylindrical formation of the implant 1, which is suggested but not required, the passage openings 4 are formed at the end regions, particularly over the entire cross-section of a hollow cylindrical main body 14 forming the receptacle space 2. Furthermore, protective coverings 15 are associated to the passage openings 4, particularly for protection of the inserted permeable elements 5 against external mechanical effects. An end cap-sided formation of the protective coverings 15 is particularly suggested with the cylindrical formation of the implant 1 and the face-sided passage openings 4.

After the insertion of the permeable elements 5 and application of the protective coverings 15 to the hollow cylindrical body 14 of the implant 1, the associated permeable elements 5, as well as possible support elements 8, spacers 9, and similar components, are fixed in their desired positions in the region of the passage opening 4. In particular, a shoulder 16 adapted to the inner contour of the passage opening 4 and, in this case, ring-shaped is formed in the region of each passage opening 4. The shoulder being followed by a portion 17 of the main body 14 having an enlarged internal diameter for receipt of the at least one permeable element 5 and the associated support elements 8, spacers 9, and the like. The associated protective covering 15 comprises a cylindrical protrusion 18 which is fit to the portion 17 having an enlarged internal diameter in such a way that the protrusion 18 can be inserted with a press fit into the portion 17, so that the protective covering 15, preferably without further fasteners, is affixed quasi-unremovably to the main body 14 by the press fit, with the protrusion 18 holding the permeable element 5 and/or the permeable elements 5 and, possible support elements 8, spacer 9 and the like of the associated passage opening 4 between itself and the associated shoulder 16, and thereby being fixed in the portion 17.

It is obvious, that every passage opening 4 can also have a peripheral contour which deviates from a circular shape. Then, the associated and/or inserted permeable element 5 has an external contour adapted correspondingly and/or to the respective portion 17.

The protective covering 15 comprises passageway openings 19 which have a large diameter in comparison to the pores 6, so that an at least essentially undisturbed flow through the protective covering 15 is possible. The protective coverings 15 specifically serve, in addition to fixing the permeable elements 5 and associated components provided here, primarily for the protection of the associated permeable elements 5 from mechanical effects which could lead to damage or destruction of the relatively brittle permeable elements 5.

The main body 14 and the protective coverings 15 are preferably produced from a material suitable for the body, preferably metal.

After the implant 1 is filled with the therapeutic agent 3 and the compensation agent 13 and after the passage openings 4 are closed by the permeable elements 5 and are fixed and covered by the protective coverings 15, the implant 1 is implanted. The therapeutic agent 3 or at least one active substance of the therapeutic agent 3 can then diffuse through the at least one permeable element 5, in this case through both permeable elements 5 of the passage opening 4 connected with the first space portion 11, and can exit into the body surrounding the implant 1 through the passage openings 19. Both permeable elements 5 of the first permeable opening 4 have pores 6 for this purpose, whose pore size and/or pore walls 7 is/are designed in such a way that at least essentially only diffusion of the therapeutic agent 3 or the desired active substance of the therapeutic agent 3 from the first space portion 11 of the receptacle space 2 occurs through the permeable elements 5.

In order to achieve the previously mentioned, preferably selective diffusion, the size of the pores 6 is appropriately adjusted and/or the pore walls 7 are chemically modified by means of interaction partners 20 indicated in FIG. 2. The interaction partners 20 are preferably fixed on at least some regions of the pore walls 7 and cause, for example, a hydrophobic or hydrophilic property of the pores 6 or act as functional groups, preferably in order to allow only selective passage through the permeable elements 5, i.e. to achieve essentially the effect of a semi-permeable membrane.

Amine groups, mercapto groups, carboxy groups, and hydroxy groups, and/or organically modified silanes can be considered, for example, as functional groups.

In order to compensate for the reduction of volume of the therapeutic agent 3 during progressive release of the therapeutic agent 3 or at least one active substance of the therapeutic agent 3, the permeable element 5 of the second passage opening 4, which communicates with the second space portion 12 of the receptacle space 2, is formed in such a way that at least one substance, for example water, from the body, not shown, surrounding the implant 1, can penetrate through the permeable element 5 into the second space portion 12 and, if necessary, mix with the optionally provided compensation agent 13. Depending on the formation of the permeable element 5 of the second passage opening 4, the penetration process mentioned can also take place without the compensation agent 13. In any case, the wall element 10, which is displaceably formed here, prevents any undesired dilution of the therapeutic agent 13 and is displaced according to the change in volume in the space portions 11 and 12.

The compensation agent 13 can, for example, be a solution of table salt.

It arises from the above that, in the exemplary embodiment depicted, a quasi-double osmosis occurs, the therapeutic agent 3 or at least one active substance of the therapeutic agent 3 exits the receptacle space 2 on the one hand and on the other hand, a suitable substance enters the receptacle space 2 through the second passage opening 4/the permeable element 5 associated therewith.

It further arises from the above that, at least essentially, only diffusion of a suitable substance from the body (not shown) surrounding the implant 1 into the second space portion 12 takes place. In particular, the permeable element 5 on this entrance side (left side in FIG. 1) is therefore designed differently than the at least one permeable element 5 on the exit side (right side in FIG. 1)—in particular in regard to pore size, pore density, and chemical modification of the pore walls 7. In the following, exemplary embodiments related to this will be described in more detail.

The polarity of the pores 6 can be ideally varied by the use of, e.g., organically modified silanes. Furthermore, the exit speed of the substance to be released from the implant 1—the therapeutic agent 3 or at least one active substance of the therapeutic agent 3—can be controlled by the pore size, pore density, and chemical modification of the pore walls 7.

If a hydrophobic substance with a higher dosage, such as steroids, tricyclic antidepressants, or the like, is to be released from the implant 1, large pores 6 with a hydrophobic internal coating are provided on the exit side and small pores 6 with a hydrophilic internal coating for the absorption of water are provided on the entrance side.

If a hydrophobic substance with a lower dosage is to be released from the implant 1, smaller pores 6 are correspondingly provided.

If a hydrophilic substance with a higher dosage is to be released from implant 1, preferably large, hydrophilic pores 6 are provided on the exit side and small, hydrophilic pores 6 are provided on the entrance side for the absorption of water.

Instead of the open-pored permeable elements 5 which are preferably provided, the second space portion 12/the second passage opening 4 can also be associated with a separating element which is not open-pored, such as a pore-free membrane, for example one that is semipermeable, through which a substance interchange can occur.

Optionally, the wall element 10 can also be left out completely if the dilution of the therapeutic agent 3 is non-critical, for example if the diffusion of a desired active substance through the permeable element 5 from the receptacle space 2 to the outside, at least essentially, is not influenced by dilution. Thus, the receptacle space 2 is not divided in this case. The compensation agent 13 can then correspondingly be left out.

On the other hand, if the wall element 10 has a sufficient sealing effect, for example in the form of a flexible membrane or a bellows, the implant 1 can allow free flow in the region of the second passage opening 4 in and out of the second space portion 12 through the passageway openings 19, i.e. the permeable element 5 inserted in the second passage opening 4 can thus be left out, so that the volume of the first space portion 11 can adjust itself freely and as necessary to the volume of the therapeutic agent 3 by appropriate displacement and/or deformation of the wall element 10.

According to a further alternative embodiment, the wall element 10 can form an external wall of the implant 1/receptacle space 2 particularly if it is flexibly formed. In this case, the second space portion 12, the second passage opening 4 with the associated permeable element 5 and the associated protective covering 15 can be left out completely.

Possibly, one passage opening 4 having at least one associated permeable element 5 can also be sufficient even if the formation of the receptacle space 2 is at least essentially rigid, i.e. the volume of the receptacle space 2 is essentially unchangeable. In this case, on one hand, the therapeutic agent 3 or at least one active substance of the therapeutic agent 3 can diffuse out of the receptacle space 2 through the permeable element 5 and, on the other hand, a substance, for example water, can diffuse from the body surrounding the implant 1 into the receptacle space 2 through the permeable element 5. In order to allow this entrance and exit through the same permeable element 5, a certain number of pores 6 are preferably designed differently and/or are chemically modified differently compared to the other pores 6.

Alternatively, however, entrance and exit can also occur only with uniformly formed and/or chemically modified pores 6.

In addition, two permeable elements 5 positioned next to one another, i.e. in parallel, of differing formation can also be associated to one passage opening 4.

If the volume of the receptacle space 2 is unchangeable, it is essential that the pressure strain on the relatively brittle permeable element 5 is kept to a minimum. Accordingly, an appropriate equilibrium of the volume flows in the exit and entrance directions is to be provided. This applies both for only one passage opening 4, and for multiple passage openings 4 with optional division by a wall element 10, as shown in FIG. 1.

If necessary, the implant 1 can also comprise a septum 21, as indicated in FIG. 1. The septum 21 can serve for initial filling and/or refilling of the therapeutic agent 3 or the compensation agent 13. Optionally, two or more septa 21 can also be provided.

The septum 21 is an element, already known from prior art, having a membrane 22 which can be penetrated by an appropriately tailored cannula for filling and/or refilling of the receptacle space 2 and which subsequently tightly reseals itself If necessary, the pores 6, particularly on the external side of the permeable element 5, can be temporarily covered for protective reasons, particularly during long storage of the implant 1, for example by a covering which is manually removable or which automatically removes itself in the implanted state. A sterile film is, for example, particularly suitable for this purpose.

What is claimed is:

1. An implant comprising:
   a body defining a receptacle space for storing an agent which is at least one of therapeutic and contains at least one active substance, said receptacle space having at least one passage opening in which a permeable element is inserted and through which the agent can leave the receptacle space,
   wherein said permeable element comprises a diffusion element having open pores with at least one of a size and pore walls which allow, at least essentially, only diffusion of at least one of the agent and at least one active substance of the agent through the diffusion element, without allowing any free flow through the permeable element,
   wherein said permeable element is composed at least essentially of an anodized material, said anodized material comprising at least one of aluminum oxide, magnesium oxide, tantalum oxide, iron oxide, tungsten oxide and titanium oxide.

2. The implant according to claim 1, wherein said permeable element comprises open pores with pore walls which are chemically modified at least regionally in order to interact with at least one of the agent, at least one active substance of the agent and externally present substances with regard to the passage through the permeable element.

3. The implant according to claim 2, wherein said permeable element comprises a membrane or film.

4. The implant according to claim 2, wherein said permeable element has an essentially uniform thickness, said uniform thickness reaching a maximum of 50 µm.

5. The implant according to claim 4, wherein said uniform thickness has a maximum of 5 µm.

6. The implant according to claim 1, wherein said permeable element is two-dimensionally supported by at least one grate-shaped support element.

7. The implant according to claim 4, wherein said permeable element is held between two grate-shaped support elements.

8. The implant according to claim 1, further comprising a second permeable element, both of said permeable elements being disposed concurrently in said at least one opening.

9. The implant according to claim 1, wherein said open pores have at least one of an essentially uniform distribution and a surface density of $10^8$ to $10^{11}/cm^2$ over the permeable element.

10. The implant according to claim 9, wherein said open pores have at least one of an essentially cylindrical form, an essentially uniform shape, an orientation that runs through the permeable element essentially perpendicularly to a plane of extension of the permeable element and portions with at least one of differing, widening and narrowing cross-sections.

11. The implant according to claim 1, wherein said open pores have at least one of an essentially cylindrical form, an essentially uniform shape, an orientation that runs through the permeable element essentially perpendicularly to a plane of extension of the permeable element and portions with at least one of differing, widening and narrowing cross-sections.

12. The implant according to claim 1, wherein said open pores have an average diameter of less than 500 nm.

13. The implant according to claim 12, wherein said open pores have an average diameter of less than 250 nm.

14. The implant according to claim 13, wherein said open pores have an average diameter between 20 nm to 250 nm.

15. The implant according to claim 1, wherein said pore walls are at least regionally formed hydrophilically or hydrophobically.

16. The implant according to claim 15, wherein said pore walls are at least regionally provided with functional groups.

17. The implant according to claim 1, wherein said pore walls are at least regionally provided with functional groups.

18. The implant according to claim 17, wherein said functional groups comprise at least one group selected from the group consisting of amine groups, mercapto groups, carboxy groups, hydroxy groups, and organically modified silanes.

19. The implant according to claim 1, wherein said body comprises at least one of a flexible wall and a movable wall element for delimiting said receptacle space so that the volume of said receptacle space is variable according to a reduction of the volume of the agent located therein.

20. The implant according to claim 19, wherein said body comprises at least one of a flexible wall element and a movable wall element which divides the receptacle space into a first space portion for storing said agent, said first space portion being in fluid communication with said first passage opening, said body further comprising a second space portion for storing a compensation agent, said second space portion being in fluid communicating with a second passage opening so that the volume of said first space portion is variable in accordance with a reduction of the volume of said agent stored therein.

21. The implant according to claim 20, wherein said wall element comprises at least one of a membrane, a bellows and a piston so as to be displaceable in said receptacle space.

22. The implant according to claim 1, wherein said body comprises two separate passage openings which respectively open said receptacle space to the atmosphere.

23. The implant according to claim 1, further comprising two separate openings which outwardly open the receptacle space; wherein a first permeable element is disposed in a first of said two separate openings and a semi-permeable membrane or a second permeable element is inserted into a second of said two passage openings and are formed so as to interact with at least one of said agent, said at least one active substance of the agent and said externally located substances such that said at least one of said agent, said at least one active substance of the agent and said externally located substances can leave said receptacle space through said first permeable element and at least one fluid can penetrate into the receptacle space through said semi-permeable membrane or second permeable element.

24. The implant according to claim 1, wherein said body comprises an oblong, essentially cylindrical main body, a protective covering disposed over said permeable element, and at least one septum in fluid communication with at least one of said receptacle space and at least one space portion of said receptacle space.

25. The implant according to claim 1, wherein said body comprises an oblong, essentially cylindrical main body, wherein said at least one passage opening is formed on an outer face of said main body and a protective covering is removably inserted into said passage opening.

26. An implant comprising:
   a body defining a receptacle space for holding a then agent which is at least one of therapeutic and contains at least one active substance, said receptacle space having at least one passage opening in which a permeable element is inserted and through which the agent can leave the receptacle space,
   wherein said permeable element comprises a diffusion element having open pores with at least one of a size and pore walls which allows, at least essentially, only diffusion of at least one of the agent and at least one active substance of the agent through the diffusion element, without allowing any free flow through the permeable element, said pore walls being chemically modified at least regionally in order to interact with at least one of the agent and at least one active substance of the agent and/or with externally present substances with regard to the passage through the permeable element,
   wherein said permeable element is composed of an anodized material comprising at least one of aluminum oxide, magnesium oxide, tantalum oxide, iron oxide, tungsten oxide and titanium oxide.

* * * * *